United States Patent [19]
Brown

[11] Patent Number: 5,740,556
[45] Date of Patent: Apr. 21, 1998

[54] FOREHEAD PERSPIRATION COLLECTOR/ DISCHARGER

[76] Inventor: Robert L. Brown, 4800 W. Anton Rd., Tucson, Ariz. 85746

[21] Appl. No.: 697,479

[22] Filed: Aug. 26, 1996

Related U.S. Application Data

[63] Continuation-in-part of Ser. No. 565,831, Dec. 1, 1995, abandoned.

[51] Int. Cl.$^6$ .............................. A41D 20/00; A61F 9/02
[52] U.S. Cl. ................. 2/181; 2/181.6; 2/452; 2/DIG. 11
[58] Field of Search .............. 2/181, 181.2, 181.6, 2/181.8, 182.8, 174, DIG. 11, 171.2, 171.3, 7, 424, 425, 10, 11, 15, 171, 452, 426, 453, 439

[56] References Cited

U.S. PATENT DOCUMENTS

| | | | |
|---|---|---|---|
| 1,084,596 | 1/1914 | Alexander | 2/181 |
| 4,130,902 | 12/1978 | Mackenroth, III et al. | 2/171.2 |
| 4,393,519 | 7/1983 | Nicastro | 2/12 |
| 4,616,367 | 10/1986 | Jean, Jr. et al. | 2/452 |
| 4,621,378 | 11/1986 | Hatchman | 2/9 |
| 4,626,247 | 12/1986 | Frankel | 2/181.8 |
| 4,638,512 | 1/1987 | Frankel | 2/DIG. 11 |
| 4,742,581 | 5/1988 | Rosenthal | 2/181 |
| 4,856,116 | 8/1989 | Sullivan | 2/DIG. 11 |
| 4,885,808 | 12/1989 | Carpenter | 2/452 |
| 4,951,316 | 8/1990 | Moody | 2/12 |
| 4,955,087 | 9/1990 | Perez et al. | 2/12 |
| 5,007,109 | 4/1991 | Wheeler | 2/10 |
| 5,054,122 | 10/1991 | Sher | 2/181.6 |
| 5,056,163 | 10/1991 | Chou | 2/181 |
| 5,105,475 | 4/1992 | Lynd et al. | 2/10 |
| 5,105,476 | 4/1992 | Cox | 2/12 |
| 5,146,630 | 9/1992 | Richard | 2/DIG. 11 |
| 5,309,577 | 5/1994 | Buononato et al. | 2/452 |
| 5,572,745 | 11/1996 | Mainus | 2/DIG. 11 |

*Primary Examiner*—Amy B. Vanatta

[57] ABSTRACT

Headgear being an absorbing forehead perspiration collector and discharge device using primarily impermeable materials comprising a soft pliable absorbing body that features a fluid barrier with absorption apertures. The extremities of the absorbing body has a junction with a pair of attachable conduit assemblies being the means for fluid discharge. The pliable absorbing body member envelops an absorbent material and when this forehead section is secured to the wearer's head utilizing its unique attachment means it serves to block and absorb forehead perspiration flow. The plug ends of the conduit assemblies are adaptable to a support means for the benefit of dark shaded lens frames. When sweaty fluids reach excessive levels in the absorbing body they flow out through the attached conduits assemblies. The conduit assemblies also serve to secure the device to the wearers head which is effectively achieved with the aid of sliding elastic cord retainers. In essence through the process of collection, absorption and discharge the complete assembly offers a new approach to dealing with annoying forehead perspiration.

16 Claims, 3 Drawing Sheets

FOREHEAD PERSPIRATION COLLECTOR/ DISCHARGER

This application is a continuation-in-part of application Ser. No. 08/565.831 filed Dec. 1, 1995, now abandoned.

BACKGROUND OF THE PRESENT INVENTION

This invention relates to equipment designed for absorption of forehead perspiration that also features separable eye lens frames. It is intended for use where conditions or activities are conducive to the causes of forehead perspiration. This invention through the use of impermeable materials and absorbing apertures allows perspired forehead fluids to become accumulated in an impermeable body and then become expelled in a less annoying location.

BACKGROUND—DESCRIPTION OF PRIOR ART

Each day somewhere in the world people hard at work under nature's elements or just involved in the outdoors find humid conditions getting the best of their activity due to profuse forehead perspiration. The outdoor person, athlete, or anyone who finds themselves active in conditions that cause profuse forehead perspiration are desirous of new technology that will assist them in a comfortable effective control of forehead perspiration. What is presently available are articles that are nearly all similar in that they consist of absorbent cloth materials placed directly against the forehead for the purpose of absorbing flowing perspiration. Those in demand of such a product would be desirous of something more effective, comfortable and attractive that would fore go the sensation of a saturated cloth around their forehead. Most people will use a shirt sleeve, a handy cloth, or even their bare hand to rid their forehead of flowing perspiration. Novel technology seems to be narrowly focused in the field of forehead perspiration absorption. There are types of articles conceived to address the problem of forehead perspiration, but don't fully satisfy what is wanted and needed.

One such article illustrates a common form of an absorbent sweatband consisting of a cotton material that encircles the head and is designed around rigid conventional style glasses. Cloth sweatbands must be periodically laundered to maintain an acceptable degree of sanitation.

Another type of device consists only of a heavy absorption sweat band consisting of traditional liquid absorbing qualities typical of cloths and fabrics that come in direct contact with the forehead secured by velcro. Eye protection from bright sunlight would require the addition of traditional shaded eye wear.

Another apparatus appears to be a device designed for face protection from airborne flying debris as well as including a moisture absorbing sweat band. It is similar to other examples in its art category and requires the same maintenance applications for a sanitary use. The effectiveness of traditional sweat bands is dependant upon the time and rate it will absorb until saturation is reached. This article does not appear to offer any satisfaction in aesthetics and may be to cumbersome to find a convenient place to carry handily.

Another device illustrates a plastic headband with a fabric sweatband and comprises a moveable shaded lens that may serve as a visor in the up position or a lens in the down position. It appears more compact than some of the aforementioned art but again utilizes common sweat absorbing fabrics designed to come into direct contact with the skin of the forehead. It also forces its user to choose its function as either a visor or a lens at any given time.

Another example describes an absorbent band with a flip up lens, again the band being cloth absorbent material.

SUMMARY OF THE INVENTION

This invention is comprised of a number of members which primarily consist of a tubular absorbing body composed of an impermeable substance, an absorbent medium and its cover, a number of fluid discharging members and its securing means. The device also has a means to accommodate sunglasses and a method to comfortably adjust said article to the wearers head.

The absorbing body consists of an impermeable material that is soft and flexible such as found in a number of PVC formulated hoses such as one known as, "Tygon 1000". Certain rubbers such as, "Latex", could also be used. Given a absorbing body section long enough to overlay transversely the frontal portion of a wearers forehead the absorbing body would have a series of apertures placed upon it in a lengthwise direction. These apertures would be in several staggered rows in a longitudinal direction with the absorbing body, thus said apertures being stratified staggered rows. The apertures run parallel and adjacent to a fluid barrier. The fluid barrier acts as a liquid seal when the absorbing body is upon the forehead in a compressive state, since the absorbing body is tubular and resilient its external surface inherently contains a natural sealing function. The size of the apertures are important to consider in order for the device to be effective. If the apertures are to small normal gravitational forces are insufficient to allow certain fluids to pass through the openings unimpeded. The minimal size for each aperture diametrically would be about five thirty seconds of an inch to achieve a constant absorbent rate through the apertures. These apertures give the body a means to draw in fluids thereby enabling the member to be an absorbing body. Upon the upper acclivity above the apertures a degree of a wall separation would be applied in a longitudinal path. This wall split would not extend the entire length of the body, it would only be long enough to allow the insertion and extraction of an absorbent material such as synthetic sponges like, "polyvinyl alcohol" or "polyurathane". The main effective ingredient in baby diapers known as, "Sodium Polyacrylate", in conjunction with other organics could also be used. The purpose of the absorbent material is to capture and store preliminary amounts of flowing perspiration which allows the device to be worn by the user for a period of time before the unit has a need to begin expelling quantities of accumulated perspiration. The length of time it will take for the absorbing body to become saturated will of course depend on a number of variables that will consider atmospheric conditions, users activity and perspiration rate. The absorbent element in this case is contained by a sleeve or cover. The cover could be composed of any material having pliable characteristics that would serve to uniformly contain the absorbent material. All members of the embodiment are impermeable in composition except for the absorbent material and perhaps parts of the elastic cord. The end openings of the absorbing body tube would be joined to a pair of impermeable resilient plugs composed of a rubber material like neoprene in which the outside configuration of the plug is such that it is snugly fitted to the internal canal size of the absorbing body. The plugs also have a larger diameter head on one end. The head of each plug serves to securely hold various members of the device in position while also limiting the extent of the plugs reach into the absorbing body. There would also be an impermeable washer slightly larger in diameter then the absorbing body and it would be seated over and against the plugs head thereby sandwiched between the plug head and the absorbing body end. This washer seat would serve to prevent fluids from running along the trough of the absorbing body and spilling out the extreme ends because it provides for a barrier between the forehead skin and the absorbing bodies external surface. The plugs have a central opening running through their length for the insertion of drain tubes which will be referred to as conduits. Once these rather elongated conduits have been inserted through the plugs central opening to a desired measure a keeper sleeve is placed over the conduits. These keepers will rest against the plugs stem end to prevent the conduits from slipping. Next a short tubular piece having an angle on one end is placed over the conduit tip to aid in fluid collection. When properly assembled these fluid collector tubes will have some contact with the absorbent material. The conduits serving as the means to drain excess sweaty fluids from the absorbing body also serve as a means for securing the device to a wearers head. These conduits being arm like members each pass along the side of the head and above the ears in a fashion similar to conventional sunglass arm appendages except that they are longer and extend past the back of the head. Next a pair of short ferrule members being slidable cord retainers each having an angle on one end and composed of any of a variety of rubber or PVC materials, incorporating a prescribed configuration of internal channels being radially positioned around a central opening are then placed over the conduits. A short piece of small diameter stretch cord is then threaded through a channel of each ferrule thereby joining the two conduits at the back of the wearers head. Next a pair of cord clips are fastened to each end of the elastic cord to prevent the cord ends from fraying. Then a pair of rubber sleeves serving as keepers, one for each ferrule, are placed over each conduit end and pressed against the cord retaining ferrule to prevent them from slipping. Short lengths of rubber hose serving as nozzles are then placed on the outlet ends of the conduits to provide for a safer terminus. With the absorbing body, (or forehead section as it is) having contact transversely to the wearer's lower forehead so that the absorbing apertures are compressed against the skin and having the drain conduits running along the side of the head of the wearer by sliding the cord retainers backward or forward in conjunction with minor cord adjustments the wearer can achieve a secure comfortable fit. The device has been found to stay effectively in place upon the wearers head even in the most rigorous of activities. The design of the device requires little tension between the pliable absorbing body and the adjustable rear enclosure.

OPERATION OF THE INVENTION

The headgear will be functionally ready for use when the complete article is properly secured to the wearers head utilizing the unique sliding cord retainers. Proper fit is achieved by applying the forehead section along the upper brow area with the discharge conduits laying back along the sides of the head with the nozzle ends pointing rearward. The wearer then adjusts the sliding cord retainers forward or rearward for an optimum degree of tension.

The device functions by entrapping perspiration that is flowing down the forehead by blocking fluids that come into contact with an impermeable barrier. This barrier can be thought of as a seal as it overlays the forehead of the user and is an inherent quality of the forehead section. One must realize that the fluid barrier and the apertures being contiguous act simultaneously at the task of damming and absorption. When the absorbing body is under a compressive state against the forehead as when in use the absorbing aperture field will overlap the fluid barrier zone. Since the body is tubular in shape and its composition is host to a number of ideal qualities as previously mentioned its form adapts to the forehead to form a fluid barrier with light pressure from the securing means. When flowing sweaty fluids are moving over the forehead they will contact the barrier of the absorbing body and be taken into the body by the absorbing apertures. Flowing perspiration passes through these apertures located in the absorbing body and becomes diffused within the body until concentrated fluids penetrate the openings of the cover sleeve and become absorbed by the absorbent material. The purpose of the inner absorbent material is to sustain the fluids that it comes into contact with. When the fluid levels rise within the absorbing body the fluids will be introduced to the inlet canals of the conduit members via the collector sleeves and travel through the conduits internal canals until such fluids become gravitationally expelled from the nozzle ends at the rear of the head.

OBJECTS AND ADVANTAGES

The object of my invention is to provide a new type of forehead perspiration accumulator that will utilize the concepts of absorption, collection, and discharge of forehead perspiration by transferring sweaty fluids through impermeable members bearing absorbing openings or apertures and channels that transmit fluid movement within and through itself in an effective and desirable manner. Accordingly it is an object of the present invention to provide a device that affords a method of absorption and fluid sustainment of forehead perspiration while also offering a means for the device to expel unwanted volumes.

Another object of the invention is to provide a device that offers a greater degree of sanitation than what is currently available by confining sweaty fluids within an impermeable body.

Another object of my invention is to provide an effective facial perspiration collecting system that can be manufactured to be aesthetically pleasing that features a useable option of attachable sunglasses.

Another object of my invention is to provide a system that offers the capability of extraction and insertion of the absorbent medium from the absorbing body for the purpose of reconditioning the absorbent material.

Another object of my invention is to produce a technologically advanced forehead perspiration collection device that can be manufactured complete using standard tooling processes such as die cut parts or can be made to assume more elegant designs that are traditional in injection molded parts.

Another object of my invention is to create a comfortable manner in which to attach headgear using slidably adjustable cord retainers.

Readers will further understand the embodiment and advantages of the invention from the detailed drawings and ensuing description.

DESCRIPTION OF THE DRAWING FIGURES

DRAWING REFERENCE NUMERALS

Figure 1:
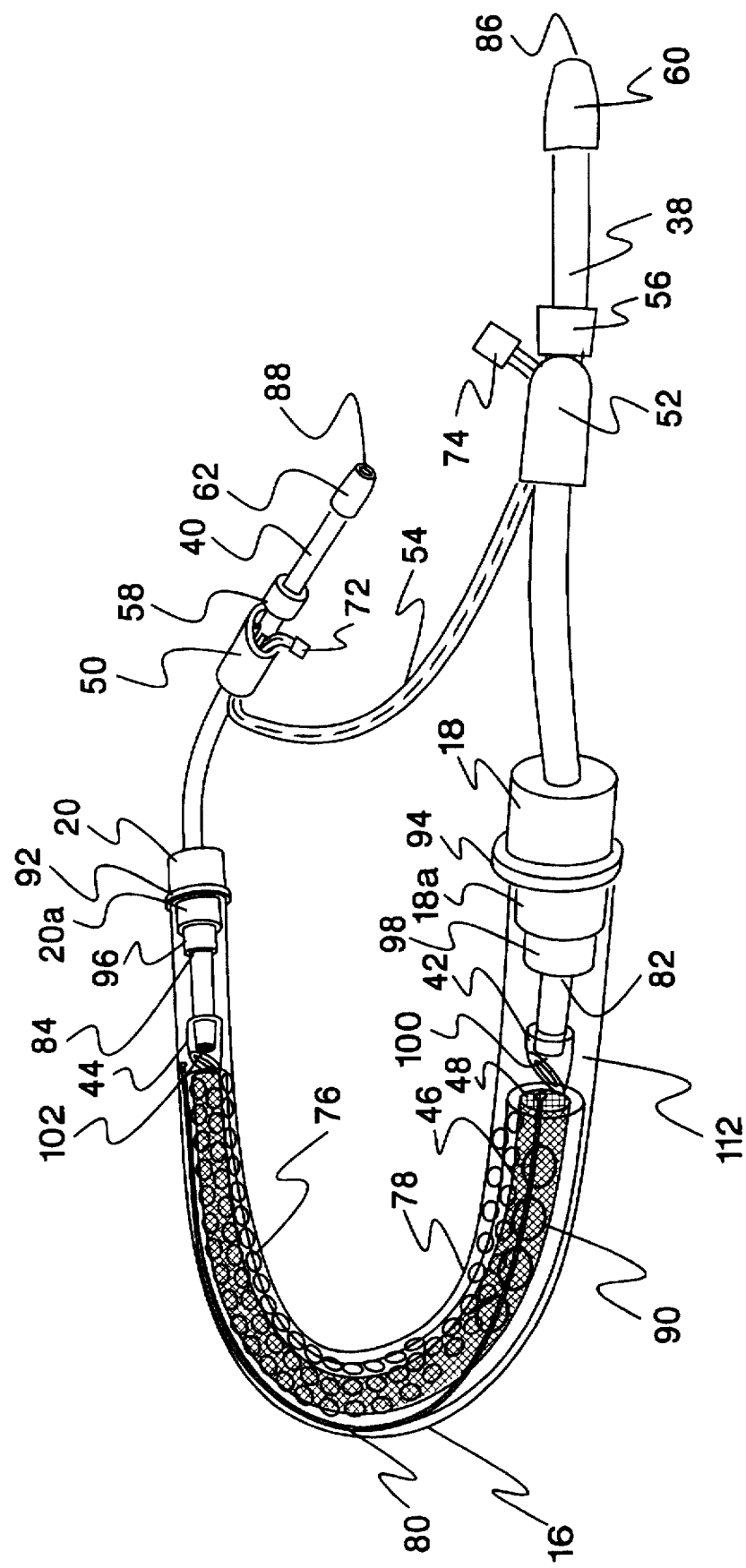
FIG. 1 illustrates the embodiment without the lens frame assembly.

16: absorbing body (forehead section)
18: plug

18a: plug stem
20: plug
20a: plug stem
22: retaining support
24: retaining support
26: connector mount
28: connector mount
30: retaining ring
32: retaining ring
34: retaining ring
36: retaining ring
38: conduit
40: conduit
42: collecting tube
44: collecting tube
46: containment cover
48: absorbent material
50: slidable cord retainer
52: slidable cord retainer
54: elastic cord
56: keeper sleeve
58: keeper sleeve
60: nozzle
62: nozzle
64: lens frame
66: frame stem
68: frame stem
70: lens
72: cord clip
74: cord clip
76: absorbing apertures
78: fluid barrier
80: wall separation
82: plug canal
84: plug canal
86: nozzle canal
88: nozzle canal
90: cover aperture
92: washer seal
94: washer seal
96: conduit keeper
98: conduit keeper
100: conduit canal
102: conduit canal
104: support opening (plug)
106: support opening (plug)
108: mount opening (ferrule)
110: mount opening (ferrule)
112: absorbing body canal

DESCRIPTION OF THE INVENTION

Referring now to the drawings, FIG. 1 illustrates the effective embodiment assembly wherein absorbing body tube 16, is an impermeable material such as, "Tygon" tubing, or Latex. In this example it is approximately 0.875 of an inch in diameter and long enough to bridge a humans frontal forehead area. The internal canal diameter of the body tube 16, in this example is approximately 0.500 of an inch. Absorbing body tube 16, also has a separation 80, in its upper wall as well as a pattern of absorbing apertures 76, that extend in several rows along the length of the tube. These absorbing apertures are staggered from one row to the next in order to create a more effectively efficient barrier for absorption. Body Tube 16, is the central host member by which the majority of members are joined. Fluid barrier 78 is not a defined object separate from its host body 16, but merely an inherent feature within the absorbing body due to its tubular shape having a circular or oval wall. This liquid barrier is primarily below the region of the absorbing apertures 76, but not necessarily outside their domain when the tube is in a compressive state as when in use. Absorbent material 48, being a substance known to have high fluid absorbing capabilities such as a synthetic sponge like, "polyvinyl alcohol" or "polyurathane" would be contained inside tubular cover 46. A baby diaper ingredient also known as "sodium polyacrylate", being an extremely effective absorbing agent could be another consideration for such an application. Cover 46, would be constructed of a highly pliable material such as "Tygon", or rubber having thin walls and bearing a number of apertures 90, where said apertures will allow sweaty fluids an entry point for absorption by absorbent material 48. Cover 46, containing absorbing material 48, is inserted or extracted through wall separation 80, of body tube 16, thereby having said members 46 and 48 resting within the body canal 112, of body tube 16. Moving further along the assembly process conduits 38 and 40 are composed of common PVC materials in this example and are inserted through openings 82 and 84 of conduit keepers 96 and 98 and plugs 18 and 20. These keepers help prevent the conduits from being pulled out of the plugs central opening or canal. Seal washers 92 and 94 being a rubber like material are then placed over plug stems 18a and 20a against the plugs heads. These seals being connectively sandwiched between the plugs heads and the absorbing body tubes ends prevent any sweaty liquids from running out of this trough area and running down the sides of the face. The collector tubes 42 and 44 are positioned on the conduit ends whereby they will have contact with absorbent material 48. The collector tubes 42 and 44 have angular ends on one side to enable the conduit to make contact with the absorbent material 48 without blocking off conduit openings 100 and 102. The conduit keepers 96 and 98, seal washers 92 and 94, plugs 18 and 20 as well as the collector tubes 42 and 44 would be made of resilient materials like natural or synthetic rubbers. "Neoprene" or "Latex" could be some examples that are resilient and impervious to the types of liquids this device would encounter. The plugs 18 and 20 having attached to them the above pertinent members are ready to be inserted into the absorbing body tube 16 end openings. The plugs stems 18a and 20a are of such a diameter that when they are inserted into the body tubes 16, end openings they will exert a sufficient amount of expanded dilation that the plugs 18 and 20 will remain in place even under a degree of extractive force that is naturally exerted by the wearer of the device. With the two conduit assemblies properly in place the collector tips 42 and 44 should be making contact with the absorbent material 48, resting within the absorbing body tube 16 and the plugs heads 18 and 20 should be firmly seated against the body tubes terminal surfaces. Ferrules 50 and 52 being slidable cord retainers are then placed over each of the conduits 38 and 40 at the fluid discharge ends 86 and 88. These ferrules have internal longitudinal channels extending around a circular lengthwise opening located in its center. The ferrules will slide along the conduits surface because its central opening is sizably the same as the exterior circumference of the conduits. The length wise channels in these slidable ferrules provide a depository cavity for an elastic cord 54, which when joined between ferrules provides for an adjustable enclosure means at the rear of a wearers head. The sliding ferrules or cord retainers as they essentially are can be moved forward or rearward to attain a comfortable fit. Elastic cord 54 can also be manipulated by pulling from the ends or the center of the cord to fine tune the cords tautness. Cord clips 72 and 74 are placed on the ends of the elastic cord 54 to prevent the cords extremities from fraying. Each of the keeper stops 56 and 58 are placed over each conduit with each keeper being slidably moveable along said conduits external surface. The purpose of the keeper stops is to prevent any slippage of the sliding cord retainers 50 and 52 once they are favorably positioned. Nozzles 60 and 62 made of a soft impermeable material like rubber are then placed over the conduits ends to define the conduits terminus as well as provide for a safer exit.

Figure 2:
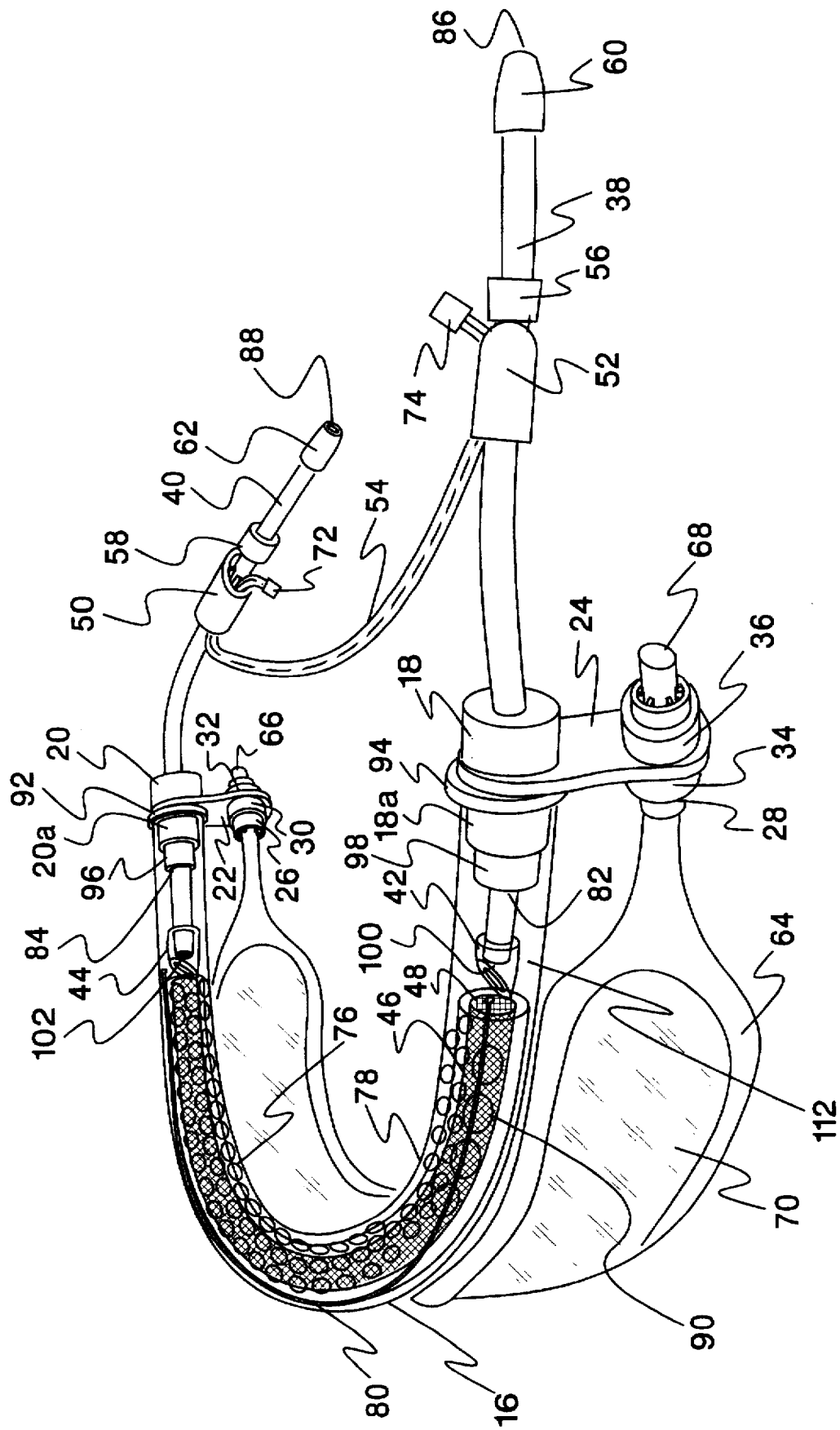
FIG. 2 shows a complete assembly with the lens frame members.
Figure 3:
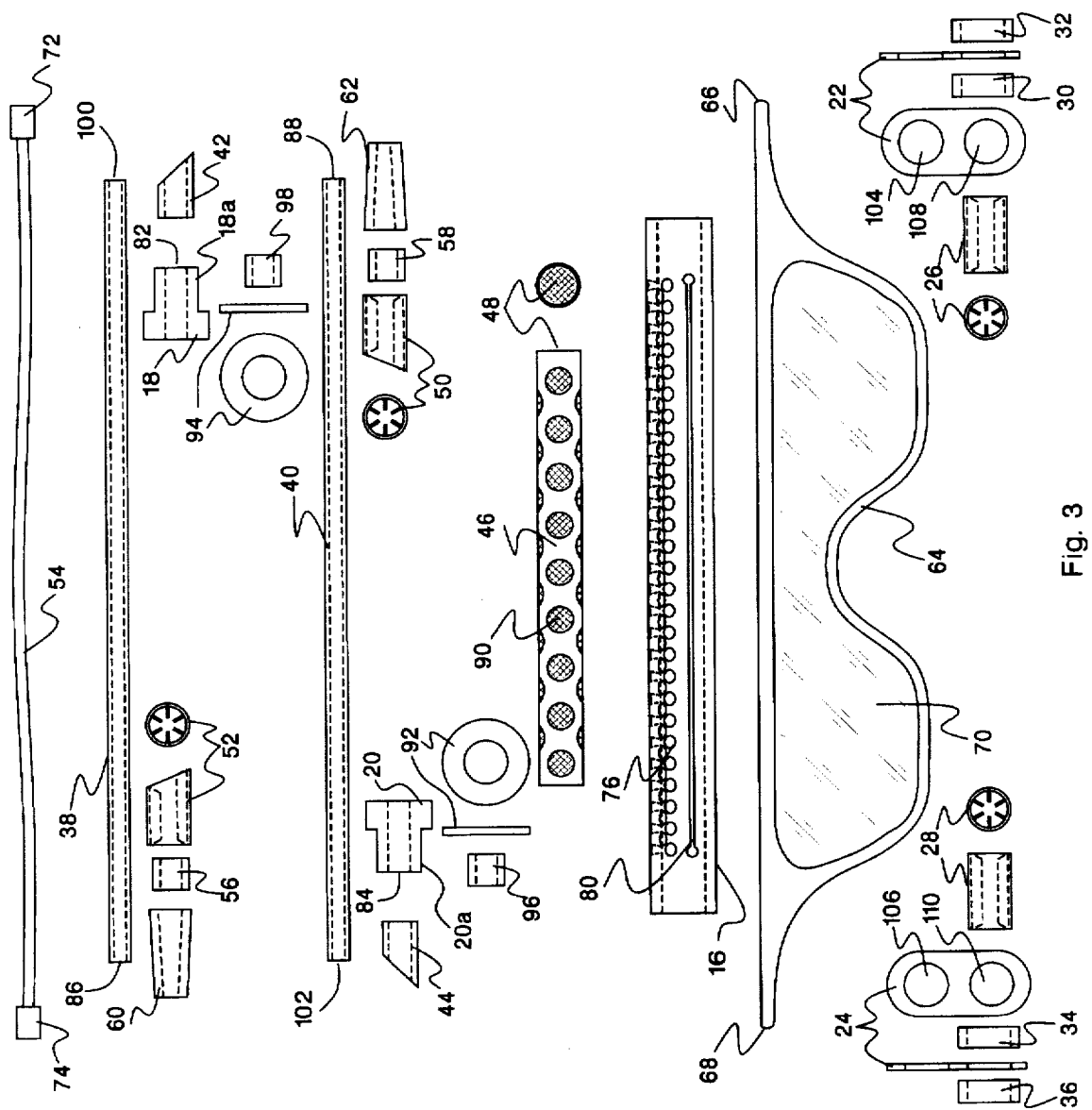
FIG. 3 shows a detailed view of the assemblies parts.

Thus having described the effective part of the embodiment as set forth in FIG. 1. FIG. 2 shows the same device with the addition of a dark shaded sunglass frame and the members by which it is attached. Recalling previously mentioned material the plugs 18 and 20 can be removed from body tube 16 at any time by just pulling the plugs out or pressing them back in. Plug stems 18a and 20a FIG.3, are inserted through openings 104 and 106 in members 22 and 24. The plugs 18 and 20 are then pressed back into the body tube 16 end openings as shown in FIG. 2. Referring to FIG. 2, parts 26 and 28 are cylindrical members having internal channels with a central opening. They are of the same material as members 50 and 52 being ready manufactured ferrule tubing having the configuration so described. These ferrule mounts are snugly inserted in openings 108 and 110 of parts 22 and 24, FIG. 3. Retaining rings 30 and 32 are each placed over one end of connector mount 26 and pressed against part 22 support retainer thereby securely holding said members in place. The same procedure is performed to the other side of the assembly involving members connector mount 28, support retainer 24, and retaining rings 34 and 36. Completing the assembly frame stems 66 and 68 are inserted into the central openings of connector mount 26 and 28 to hold the lens frame 64 having a dark shaded lens 70 in place.

SCOPE OF THE INVENTION

Modifications in design and construction could produce other effects. One might imagine other uses such a device could satisfy. The present inventions purpose is to satisfy the universal desire by people to achieve an effective and aesthetically pleasing alternative to conventional sweat bands and crude sweat absorbing materials. Complete listings of potential users could be cited but broad categories would include outdoor recreationists, physical fitness buffs, athletes, surgeons, military combat personal or anyone confronted with the conditions that cause perspiration.

While the above description contains many specificities, the reader should not interpret these as limitations on the scope of the invention, but merely as exemplifications of preferred embodiments thereof. Those skilled in the art will envision many other possible variations are within its scope. For example skilled artisans will readily be able to change the dimensions and shapes of the various embodiments. In lieu of readily available manufactured components to assemble the main embodiment they will be able to fabricate attractive brightly colored bodies through modern manufacturing practices. Thermo heat forming, injection molding and extrusion in consideration with modern materials such as polymers and resins both synthetic and natural are examples of processes and engineering steps that could lead to more comfortable and aesthetically pleasing embodiments of the depicted drawings. They will develop new and attractive lens designs. They will manufacture the bodies of the invention featuring different shapes and sizes. They will forego the stretch cord at the back of the head and utilize any of the various similarly conventional means of headgear securement. They will add additional fluid sustaining elements or use none at all. They will experiment with different materials for the absorbing body using both resilient and rigid materials. They will create new ways to replace the absorbent medium through compartment doors instead of wall separations. They will find a number of various methods to capture flowing forehead perspiration using impermeable materials. They will find various ways to discharge excessive sweaty fluids.

In summary the reader is requested to determine the scope of the invention by the appended claims and their legal equivalents, and not by the examples which have been given.

What is claimed is:

1. Headgear device for accumulating and discharging forehead perspiration including head engaging means for removably securing said device on a wearer's head and a means for attaching an eye wear lens frame, a forehead section carried by said head engaging means in a position to extend across and upon the forehead of a wearer's head, said forehead section being substantially tubular having a longitudinal internal canal being inclusive of an opening at each end thereof, said forehead section having disposed longitudinally through a wall therein a plurality of apertures arranged in a predetermined pattern, said section having a longitudinal separation of a predetermined length through a wall of said forehead section and said section having an external fluid barrier means;

an elongated tubular cover member being substantially flexible having a plurality of apertures arranged around its circumference in a predetermined pattern, said cover having a means to contain an absorbent material;

a pair of fluid discharging assemblies, each assembly having a number of members to include an elongated conduit and a plug, said plug having a plurality of diametrically sized surfaces, said surfaces to include a stem end and a head end, said stem end having a fastening means and said head end having a diameter larger in circumference than said stem end, each said plug having a central opening extending through its length, each said opening being fitted over said conduit so that a degree of conduit extends out of said plug from the opposite end so that a fluid collector sleeve can be fitted over each intake end of said conduit and a means for embodying a fluid retaining seal to said head end of said plug;

a pair of slidable cord retainers being substantially tubular with an angular terminus on one end and having around its internal surface a plurality of longitudinal channels extending around a central opening, said opening being fitted over the external surface of each said conduit member and a length of elastic cord being threaded through one channel of each said cord retainer so that said conduit assemblies are joined and an annular keeper sleeve being fitted over said conduits to become in contact with said cord retainer, said keeper being resistive to cord retainer movement, and a pair of tubular nozzles each being affixed in position to said conduits' discharge ends;

support means for connective eyewear lens frame being inclusive of a pair of flat retaining supports each having a width and a length, said length having an arched terminus on each end, said support being substantially thin having two circular openings being arranged in opposition on a singular plane.

2. Headgear according to claim 1 wherein said forehead section is of sufficient size to transverse and overlay the frontal portion of a wearer's forehead.

3. Headgear according to claim 1 wherein said apertures of said forehead section are absorption openings thus allowing said forehead section to be an absorbing mechanism having a means to draw in fluids.

4. Headgear according to claim 1 wherein said forehead section includes a longitudinal wall separation upon the upper acclivity from said apertures of said forehead section extending in a linear parallel path to said apertures and whereby said wall separation is the means for providing the insertion or extraction of relative absorbent materials.

5. Headgear according to claim 1 wherein said conduit assemblies having plugs embodied thereto and said plugs having a fastening means to said forehead section end openings is providably a means for assembly.

6. Headgear according to claim 1 wherein said forehead section and a number of members are composed of impermeable materials having a pliable resiliency.

7. Headgear according to claim 1 wherein said forehead section has a diametrical wall surrounding a hollow interior whereby said wall provides a means along its exterior length to form a barrier seal to flowing forehead perspiration when said headgear is properly secured to a wearer's head.

8. Headgear according to claim 7 wherein said apertures of said forehead section are disposed in a predetermined array being parallel and immediately above said barrier seal with the wall separation of said forehead section facing directly up and whereby the apertures lie within the barrier seal area when the forehead section is under compressive stress when being worn upon the forehead.

9. Headgear according to claim 1 wherein said absorbent material has a high liquid retention means said absorbent material having a mass, an exterior surface and a predetermined configuration.

10. Headgear as in claim 1 wherein said apertures of said tubular cover are for the purpose of allowing accumulating forehead perspiration fluids access to said absorbent material.

11. Headgear as in claim 1 wherein said fluid retaining seals have a diametrical contour larger than said forehead section's cross sectional external contour, said fluid retaining seals being located between said plug heads and said forehead section end openings such that when said forehead section is under compressive retention upon the wearer's forehead said seals have providably dammed said forehead section extremities from any escaping fluids moving along a trough of the fluid absorption area of said forehead section formed between the wearer's forehead skin and the external surface of said forehead section.

12. Headgear according to claim 1 wherein said fluid discharging assemblies are separable from said forehead section end openings and whereby said fluid discharging assemblies when securably fastened to said forehead section end openings have a means for transferring fluids out of said forehead section through said discharging assembly conduits whereby said fluid transfer becomes expelled from discharge ends of said nozzles.

13. Headgear according to claim 1 wherein said internal longitudinal canal of said forehead section having said fluid discharging members embodied to said end openings of said forehead section has providably a means so that perspired forehead fluids can become accumulated therein until excessive amounts become discharged through said fluid discharging members.

14. Headgear comprising a fluid absorbing body being composed of an impermeable substance, said absorbing body having a predetermined configuration including a surrounding wall around a central hollow cavity and said absorbing body having a degree of an opening at each extremity thereof, said opening extending through to said hollow cavity of said absorbing body and said absorbing body having an opening means through a wall for insertion and extraction of absorbent devices, and said absorbing body having a predetermined array of wall cutouts disposed along its longitudinal surface, said cutouts being fluid absorption openings and said absorbing body providing a blocking barrier means to flowing forehead fluids coming into contact with the external surface of said absorbing body when said body is in a compressive state upon the forehead

- a pair of elongated fluid discharge members each having an adaptable connective means to each extreme end opening of said fluid absorbing body and said pair of fluid discharge members having a predetermined configuration for continuously conveying excess fluids out of said absorbing body whereby said fluids become expelled at terminus ends of said discharge members and

- a narrow rib projecting sufficiently out around the external circumference of said absorbing body at its extreme end, said rib being a fluid retaining seal providing said absorbing body a means to retain excessive amounts of forehead perspiration within an external absorption trough means of said absorbing body when said headgear is secured to the wearer's head and

- an absorbent device having a configuration to be contained within the surrounding walls of said absorbing body.

- a headgear securing means comprising said fluid discharge members and a pair of elastic cord retainers each said cord retainer having a means to retain an end of a single elastic cord, said cord having an adjustable means within said cord retainer and each said cord retainer being slidably moveable along an appendage of said fluid discharge members, said appendage being a headgear securing aid when laid flat laterally along a side of the wearer's head so that said appendage is of sufficient length to extend past the back of a wearer's head to a predetermined measure such that when said appendages are joined by said elastic cord at the back of the head, said cord is an adjustable enclosure member when said cord is drawn taut between retaining members or upon the slidable forward or rearward movement of said cord retainers providably urging a comfortable fit and

- an eyewear lens frame being a one piece structure having a substantially rigid flexibility void of any pivoting members, said frame structure having adopted a curved arch shape relative to the frontal curvature of a human face and said lens frame having a brief rod shaped arm stem located at each lens frame extremity, said frame stems each having a means to be inserted into a cylindrical connective ferrule having a central opening, said connective ferrule being embodied within an opening in a retaining support, said retaining support having its remaining opening secured to said fluid discharge member so that said lens frame is securely held within its support means.

15. Headgear as in claim 14 wherein said lens frame is removeably separable from said connective ferrule and further including a lens frame support means that is removably separable from said fluid discharge members.

16. Headgear as in claim 14 being substantially a transferring device for flowing forehead perspiration wherein external fluids become accumulated within an absorbing body so that such fluids become internally stored and whereby said fluids are transferred out through said fluid discharge members to become externally expelled.

* * * * *